(12) United States Patent
Bruhns et al.

(10) Patent No.: US 7,727,586 B2
(45) Date of Patent: Jun. 1, 2010

(54) PRODUCTION OF WATER-ABSORBING POLYMERIC PARTICLES BY DROPLETIZATION POLYMERIZATION IN THE GAS PHASE

(75) Inventors: Stefan Bruhns, Mannheim (DE); Volker Frenz, Stemwede (DE); Dennis Lösch, Altrip (DE); Volker Seidl, Mannheim (DE); Uwe Stueven, Bad Soden (DE); Carolin Nadine Dücker, Ludwigshafen (DE); Matthias Weismantel, Jossgrund-Oberndorf (DE); Wilfried Heide, Freinsheim (DE); Stefan Blei, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 76 days.

(21) Appl. No.: 11/814,021

(22) PCT Filed: Jan. 24, 2006

(86) PCT No.: PCT/EP2006/050419

§ 371 (c)(1),
(2), (4) Date: Jul. 16, 2007

(87) PCT Pub. No.: WO2006/079631

PCT Pub. Date: Aug. 3, 2006

(65) Prior Publication Data

US 2008/0188586 A1      Aug. 7, 2008

(30) Foreign Application Priority Data

Jan. 28, 2005   (DE) ................... 10-2005-004-296
Mar. 24, 2005   (DE) ................... 10-2005-014-292
Jan. 11, 2006   (DE) ................... 10-2006-001-596

(51) Int. Cl.
*C08F 2/10*   (2006.01)
*C08F 2/00*   (2006.01)
*C08F 2/01*   (2006.01)
*C08F 2/04*   (2006.01)

(52) U.S. Cl. ............... 427/213; 427/212; 427/331; 427/372.2; 250/434; 250/435; 250/436; 250/428; 250/432 R; 422/131; 422/134; 422/129; 422/213; 422/212; 526/72; 526/75; 526/317.1; 526/318.5; 502/400; 502/401; 502/402; 523/109; 523/111; 428/402; 424/400

(58) Field of Classification Search ............... 522/1; 250/434, 435, 436, 428, 432; 422/131, 134, 422/129, 213, 212; 427/331, 372.2; 526/72, 526/75, 317.1, 318.5; 502/400, 401, 402; 523/109, 111; 428/402; 424/400
See application file for complete search history.

(56) References Cited

U.S. PATENT DOCUMENTS

| | | | | |
|---|---|---|---|---|
| 5,059,664 A | * | 10/1991 | Yada et al. | .......... 526/240 |
| 5,115,011 A | * | 5/1992 | Harada et al. | .......... 524/419 |
| 5,269,980 A | | 12/1993 | Levendis et al. | |
| 5,447,727 A | * | 9/1995 | Graham | .......... 424/487 |
| 6,107,432 A | | 8/2000 | Engelhardt et al. | |
| 2006/0127585 A1 | * | 6/2006 | Himori et al. | .......... 427/372.2 |
| 2006/0217508 A1 | | 9/2006 | Schmid et al. | |
| 2007/0100115 A1 | | 5/2007 | Schmid et al. | |
| 2007/0142589 A1 | * | 6/2007 | Rogers et al. | .......... 526/303.1 |
| 2009/0192036 A1 | * | 7/2009 | Losch et al. | .......... 502/402 |

FOREIGN PATENT DOCUMENTS

| | | | |
|---|---|---|---|
| DE | 103 14 466 | | 10/2004 |
| DE | 103 40 253 | | 3/2005 |
| DE | 102004024437 | | 12/2005 |
| EP | 0 348 180 | | 12/1989 |
| EP | 1 097 946 | | 5/2001 |
| EP | 1 424 346 | | 6/2004 |
| WO | WO-96/40427 | | 12/1996 |
| WO | WO-02/066520 | | 8/2002 |
| WO | WO-2005/111088 | | 11/2005 |
| WO | WO 2007093531 A1 | * | 8/2007 |
| WO | WO 2008009598 A1 | * | 1/2008 |
| WO | WO 2008095892 A1 | * | 8/2008 |

OTHER PUBLICATIONS

Buchholz and Graham, *Modern Superabsorbent Polymer Technology*, Wiley-VCH, pp. 97-103 (1998).
International Search Report in PCT?EP2006/050419 dated Apr. 26, 2006.

* cited by examiner

*Primary Examiner*—Sanza L McClendon
(74) *Attorney, Agent, or Firm*—Marshall, Gerstein & Borun LLP

(57) ABSTRACT

A process for producing water-absorbing polymeric particles by dropletization polymerization in the gas phase, which comprises drying the polymeric particles after the polymerization in a fluidized bed, the water-absorbing polymeric particles themselves, hygiene articles comprising these water-absorbing polymeric particles and also apparatus for implementing the process.

20 Claims, 3 Drawing Sheets

PRODUCTION OF WATER-ABSORBING POLYMERIC PARTICLES BY DROPLETIZATION POLYMERIZATION IN THE GAS PHASE

CROSS-REFERENCE TO RELATED APPLICATIONS

This is the U.S. national phase application of International Application No. PCT/EP2006/050419, filed Jan. 24, 2006, which claims the benefit of German patent application No. 10 2006 001 596.7, filed Jan. 11, 2006, German patent application No. 10 2005 014 292.3, filed Mar. 24, 2005, and German patent application No. 10 2005 004 296.1, filed Jan. 28, 2005.

The present invention relates to a process for producing water-absorbing polymeric particles by dropletization polymerization in the gas phase wherein the polymeric particles are dried in a fluidized bed dryer after the polymerization, to the water-absorbing polymeric particles themselves, to hygiene articles comprising these water-absorbing polymeric particles and to apparatus for implementing the process.

Further embodiments of the present invention are discernible from the claims, the description and the examples. It will be understood that the hereinbefore mentioned and the hereinbelow still to be more particularly described features of the subject matter of the present invention are utilizable not only in the particular combination indicated but also in other combinations without departing from the realm of the invention.

The production of water-absorbing polymeric particles is described in the monograph "Modern Superabsorbent Polymer Technology", F. L. Buchholz and A. T. Graham, Wiley-VCH, 1998, pages 71 to 103.

Water-absorbing polymers are used as products capable of absorbing aqueous solutions to produce diapers, tampons, sanitary napkins and other hygiene articles, but also as water-retaining agents in market gardening.

The properties of the water-absorbing polymers can be controlled via the degree of crosslinking. Gel strength increases and absorptive capacity decreases with increasing degree of crosslinking. Consequently, as Absorbency Under Load (AUL) increases, Centrifuge Retention Capacity (CRC) decreases (although at very high degrees of crosslinking Absorbency Under Load decreases, too).

To improve their performance characteristics, for example Saline Flow Conductivity (SFC) in the diaper and Absorbency Under Load (AUL), water-absorbing polymeric particles are generally postcrosslinked. This increases only the degree of crosslinking of the particle surface, making it possible to decouple Absorbency Under Load (AUL) and Centrifuge Retention Capacity (CRC) to some extent at least. Postcrosslinking can be carried out in the aqueous gel phase. Preferably, however, ground and screened particles of the base polymer are surface coated with a postcrosslinker, dried and thermally postcrosslinked. Useful postcrosslinkers include compounds comprising at least two groups capable of forming covalent bonds with the carboxylate groups of the hydrophilic polymer.

Spray polymerization is a way to combine the polymerization and drying steps. In addition, particle size becomes controllable within certain limits through suitable process management.

The production of water-absorbing polymeric particles by spray polymerization is described for example in EP-A-0 348 180, WO-A-96/40427, DE-A-103 14 466, DE-A-103 40 253 and DE-A-102004024437.

U.S. Pat. No. 5,269,980 describes the spray polymerization and the dropletization polymerization.

The present invention has for its object to provide an improved process for producing water-absorbing polymeric particles.

Figure 1:
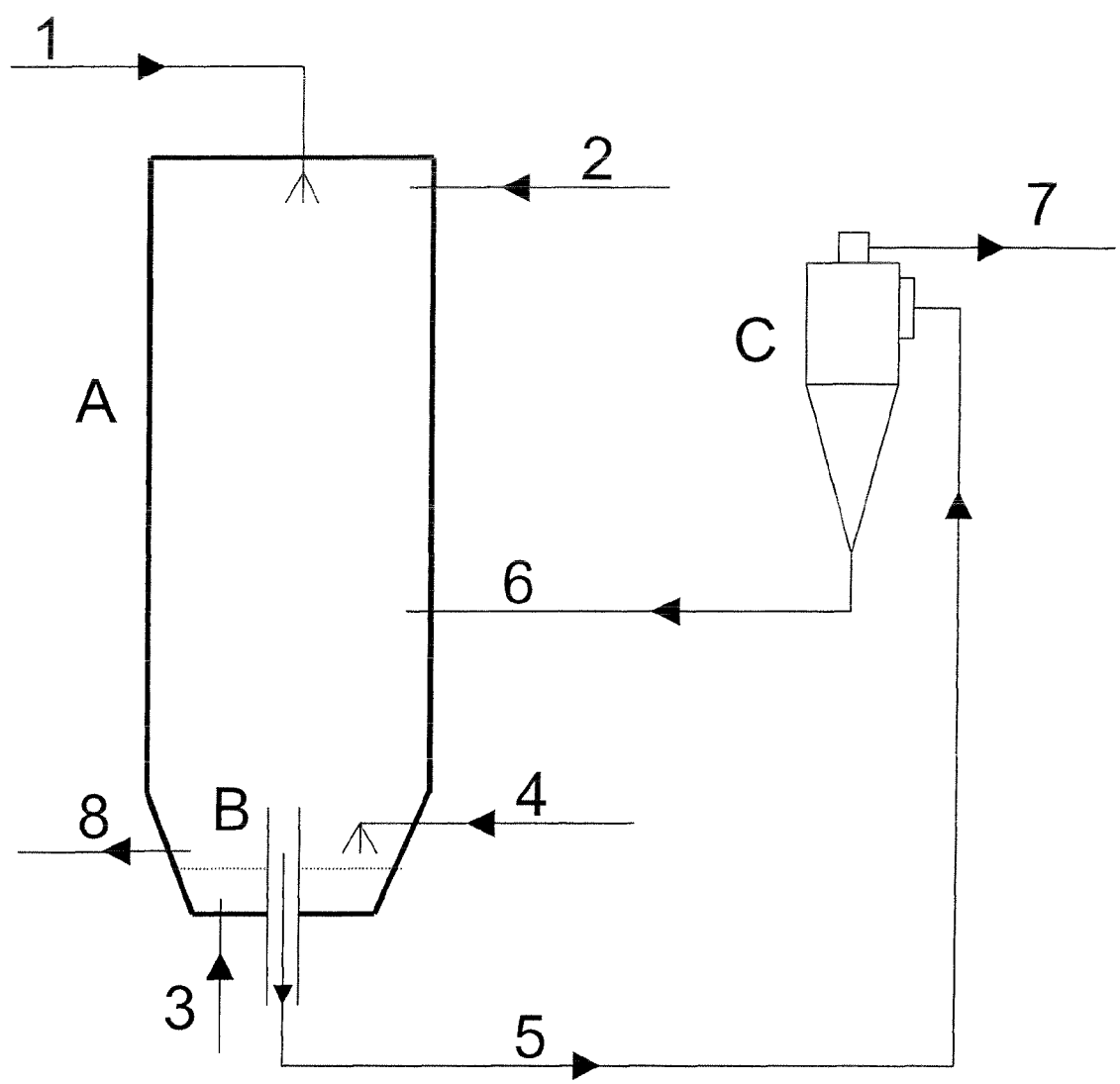
FIGS. 1 and 2 are schematics illustrating apparatus for post-treating water-absorbing polymeric particles in a fluidized bed.

We have found that this object is achieved by a process for producing water-absorbing polymeric particles by dropletization polymerization in the gas phase, which comprises the polymeric particles after the polymerization being dried and selectively agglomerated and/or postcrosslinked, the drying being carried out in a fluidized bed.

In dropletization polymerization, a monomer solution is metered into a gas phase to form droplets. The dropletization of the monomer solution can be carried out using a dropletizer plate for example.

A dropletizer plate is a plate having at least one drilled hole, the liquid passing downwardly through the drilled hole. The dropletizer plate or the liquid is set oscillating and this creates, on the underside of the dropletizer plate, one ideally monodisperse chain of droplets per drilled hole.

The number and the size of the drilled holes are chosen according to the desired capacity and droplet size. Droplet diameter is typically 1.9 times the diameter of the drilled hole. It is important that the liquid to be dropletized does not pass too quickly through the drilled hole, i.e., the pressure drop across the drilled hole is not too large. Otherwise, the liquid is not dropletized and instead the jet of liquid is torn apart (forming a spray) as a result of high kinetic energy. The speed at which the monomer solution passes through the drilled hole is preferably less than 0.2 m/s, more preferably less than 0.1 m/s and most preferably less than 0.05 m/s. The pressure drop across the drilled hole is preferably less than 1 bar, more preferably less than 0.5 bar and most preferably less than 0.3 bar.

The dropletizer plate typically has at least one, preferably at least 10, more preferably at least 50 and typically up to 10000, preferably up to 5000 and more preferably up to 1000 drilled holes, the drilled holes typically forming a uniform distribution over the dropletizer plate, preferably in the so-called triangular pitch, i.e., three drilled holes at a time form the corners of an equilateral triangle.

The diameter of the drilled holes is adapted to the desired droplet size. The diameter of the drilled holes is typically at least 50 µm, preferably at least 75 µm and more preferably at least 100 µm and typically up to 1000 µm, preferably up to 600 µm and more preferably up to 300 µm.

It may be preferable to place the dropletizer plate on a carrier plate which likewise has drilled holes. The drilled holes in the carrier plate have a larger diameter than the drilled holes in the dropletizer plate and are arranged such that each drilled hole in the dropletizer plate is above a concentric drilled hole in the carrier plate. This arrangement allows a fast change of the dropletizer plate, for example in order that droplets of another size may be generated. Such a system of dropletizer plate and carrier plate shall be deemed to be a dropletizer plate for the purposes of this invention, i.e., the underside of the dropletizer plate/carrier plate system is the underside of the dropletizer plate.

Dropletization may also be effected using pneumatic drawing dies, rotation, cutting of a jet or fast-actuable microvalve dies.

In a pneumatic drawing die, a jet of liquid is accelerated together with a gas stream through a hole diaphragm. The gas rate can be used to control the diameter of the jet of liquid and hence the droplet diameter.

In dropletization through rotation, the liquid passes through orifices in a rotating disk. The centrifugal force acting on the liquid causes droplets of defined size to be torn off.

The emerging jet of liquid can also be cut into defined segments by means of a rotating knife. Each segment subsequently forms a droplet.

When microvalve dies are used, droplets holding a defined volume of liquid are generated directly.

Polymeric particles transferring into the fluidized bed dryer, i.e., after the polymerization, have a residual monomer content of less than 20% by weight, preferably of less than 15% by weight, more preferably of less than 10% by weight and most preferably of less than 5% by weight and a water content in the range from 1% to 35% by weight, preferably in the range from 5% to 30% by weight, more preferably in the range from 10% to 25% by weight and most preferably in the range from 15% to 20% by weight. Water content is determined in accordance with EDANA (European Disposables and Nonwovens Association) recommended test method No. 430.2-02 "Moisture content". Residual monomer content is determined in accordance with EDANA (European Disposables and Nonwovens Association) recommended test method No. 410.2-02 "Residual monomers".

The process of the present invention provides water-absorbing polymeric particles possessing high Absorbency Under Load and a low fraction of extractables. More particularly, the water-absorbing polymeric particles produced by the process of the present invention have an Absorbency Under Load value after drying in the fluidized bed as is customarily not obtained until after postcrosslinking.

It is theorized that the polymerization of relatively large droplets in the gas phase produces structured polymeric particles having a pronounced shell. This shell provides high gel strength. Owing to the low crosslink density in the core, however, absorbency itself still remains high. Therefore, the water-absorbing polymeric particles produced by the process of the present invention have high absorbency under load. Mechanical stress destroys this shell and the fraction of extractables rises distinctly. When drying is too rapid, for example as a result of high temperatures in the reactor, however, the shell is torn apart by the water vapor which escapes too rapidly and the polymerization ends too quickly as a result of solvent deficiency. It is therefore important that the polymeric particles obtained by dropletization polymerization be gently afterdried.

The polymeric particles are preferably transferred in the fluidized state from the polymerization into at least one of the process steps drying, agglomeration or postcrosslinking.

Particularly preferably, the water-absorbing polymeric particles are maintained in the fluidized state at all times during transportation.

Agglomeration and postcrosslinking can be carried out in succession or concurrently. Performing agglomeration and postcrosslinking in one operation is preferred.

The transfer of the polymeric particles from the polymerization into the at least one process step drying, agglomeration or postcrosslinking in a fluidized state is not subject to any restriction.

In the fluidized state, the kinetic energy of the polymeric particles is greater than the potential for cohesion/adhesion between the polymeric particles.

The fluidized state can be achieved by means of a fluidized bed. In a fluidized bed, a suitable carrier gas is flowed upwardly through the water-absorbing polymeric particles, so that the particles form a fluidized layer. The height of the fluidized layer is controlled via gas rate and gas velocity, i.e., through the pressure drop of the fluidized layer (kinetic energy of the gas).

But the fluidized state can also be achieved by means of pneumatic conveying. In pneumatic conveying, a suitable carrier gas is flowed against the water-absorbing polymeric particles in the direction of transport. The transport in the fluidized state is likewise controlled via gas rate and gas velocity, i.e., through the kinetic energy of the gas.

In the simplest and preferred variant, the water-absorbing polymeric particles fall through a suitable connection from the previous process step directly into at least one of the process steps drying, agglomeration or postcrosslinking. The fluidized state can here be controlled within wide limits via throughput and carrier gas rate. Typically, free-falling particles have a sufficient distance from each other and a sufficient kinetic energy, so that a fluidized state exists.

Examples of suitable connections are tubes, whose diameter and inclination are such that the openings at the ends of the tube partially or completely overlap in the vertical, preferably to an extent of at least 50%, more preferably to an extent of at least 70% and most preferably to an extent of at least 90%. The connection is more preferably produced by connecting the polymerization reactor directly to the fluidized bed apparatus, i.e., by formally using a tube of length 0.

The dropletization polymerization is preferably carried out in a laminar gaseous flow. A laminar gaseous flow is a gas flow in which the individual layers of the flow do not mix but move in parallel. The Reynolds number (Re) is a measure of the flow conditions. The gas flow is laminar below a critical Reynolds number ($Re_{cri}$) of 2300. The Reynolds number of the laminar gas flow is preferably less than 2000, more preferably less than 1500 and most preferably less than 1000. The lower limiting case for the laminar inert gas flow is a quiescent inert gas atmosphere (Re=0); that is, inert gas is not fed in continuously.

Agglomeration and/or postcrosslinking are preferably carried out in the fluidized state.

For agglomeration and/or postcrosslinking, a solution comprising the agglomeration assistant and/or the postcrosslinker is sprayed onto the water-absorbing polymeric particles before thermal drying.

The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

Contact dryers are preferable, paddle dryers more preferable and disk dryers most preferable as apparatus in which thermal drying is carried out. Suitable dryers include for example Bepex® dryers and Nara® dryers. Fluidized bed dryers can be used as well.

Drying is preferably carried out in the mixer itself, for example by heating the shell or blowing warm air into it. In one particularly preferred embodiment, the solution is applied to the water-absorbing polymeric particles in a fluidized bed reactor and they are agglomerated and/or postcrosslinked in the fluidized bed reactor.

Monomer solutions useful in the process of the present invention comprise
a) at least one ethylenically unsaturated acid-functional monomer,
b) at least one crosslinker,
c) selectively one or more ethylenically and/or allylically unsaturated monomers copolymerizable with the monomer a), and
d) selectively one or more water soluble polymers onto which the monomers a), b) and if appropriate c) can be at least partly grafted.

Suitable monomers a) are for example ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Acrylic acid and methacrylic acid are particularly preferred. Acrylic acid is most preferable.

The acid groups of monomers a) are typically in a partially neutralized state, the extent of neutralization being preferably in the range from 25 to 85 mol %, more preferably in the range from 27 to 80 mol %, and even more preferably in the range from 27 to 30 mol % or from 40 to 75 mol %, for which the customary neutralizing agents can be used, preferably alkali metal hydroxides, alkali metal oxides, alkali metal carbonates or alkali metal bicarbonates and also mixtures thereof. Ammonium salts can also be used instead of alkali metal salts. Sodium and potassium are particularly preferred as alkali metals, but most preference is given to sodium hydroxide, sodium carbonate or sodium bicarbonate and also mixtures thereof. Typically, neutralization is achieved by mixing the neutralizing agent as an aqueous solution, as a melt or else preferably as a solid material into the monomer solution. For example, sodium hydroxide having a water fraction of distinctly below 50% by weight can be present as a waxy mass having a melting point above 23° C. in this case, metering as piece goods or melt at elevated temperature is possible.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

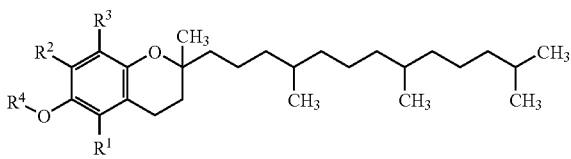

where $R^1$ is hydrogen or methyl, $R^2$ is hydrogen or methyl, $R^3$ is hydrogen or methyl and $R^4$ is hydrogen or an acyl radical of 1 to 20 carbon atoms.

Preferred $R^4$ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where $R^1=R^2=R^3=$methyl, especially racemic alpha-tocopherol. $R^1$ is more preferably hydrogen or acetyl. RRR-alpha-tocopherol is preferred in particular.

The monomer solution comprises preferably not more than 130 weight ppm, more preferably not more than 70 weight ppm, preferably not less than 10 weight ppm, more preferably not less than 30 weight ppm and especially around 50 weight ppm of hydroquinone half ether, all based on acrylic acid, with acrylic acid salts being arithmetically counted as acrylic acid. For example, the monomer solution can be produced using an acrylic acid having an appropriate hydroquinone half ether content.

The crosslinkers b) are compounds having at least two free-radically polymerizable groups which can be free-radically interpolymerized into the polymer network. Useful crosslinkers b) are for example ethylene glycol dimethacrylate, diethylene glycol diacrylate, allyl methacrylate, trimethylolpropane triacrylate, triallylamine, tetraallyloxyethane, as described in EP-A-0 530 438, di- and triacrylates as described in EP-A-0 547 847, EP-A-0 559 476, EP-A-0 632 068, WO-A-93/21237, WO-A-03/104299, WO-A-03/104300, WO-A-03/104301 and DE-A-103 31 450, mixed acrylates which, as well as acrylate groups, comprise further ethylenically unsaturated groups, as described in DE-A-103 314 56 and prior German application 10355401.7, or crosslinker mixtures as described for example in DE-A-195 43 368, DE-A-196 46 484, WO-A-90/15830 and WO-A-02/32962.

Useful crosslinkers b) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. Useful crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

However, particularly advantageous crosslinkers b) are di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixed ethoxylated or propoxylated glycerol, of 3-tuply mixed ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane.

Very particularly preferred for use as crosslinkers b) are diacrylated, dimethacrylated, triacrylated or trimethacrylated multiply ethoxylated and/or propoxylated glycerols as described for example in WO-A-03/104301. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 weight ppm) in the water-absorbing polymer and the aqueous extracts of water-absorbing polymers produced therewith have an almost unchanged surface tension compared with water at the same temperature (typically not less than 0.068 N/m).

Examples of ethylenically unsaturated monomers c) which are copolymerizable with the monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyglycols or polyacrylic acids, preferably polyvinyl alcohol and starch.

The reaction is preferably carried out in the presence of an inert carrier gas, inert meaning that the carrier gas cannot react with the constituents of the monomer solution. The inert carrier gas is preferably nitrogen. The oxygen content of the inert carrier gas is advantageously below 5% by volume, preferably below 2% by volume and more preferably below 1% by volume. The carrier gas is preferably also used for the fluidized bed apparatus and, if appropriate, the pneumatic conveying.

The inert carrier gas can be passed through the reaction space cocurrently with or countercurrently to the free-falling droplets of the monomer solution, preferably cocurrently. Preferably, some or all of the carrier gas, preferably at least 50% of the carrier gas and more preferably at least 75% of the carrier gas, is returned into the reaction space as cycle gas after one pass. Typically, some of the carrier gas and preferably up to 10% of the carrier gas, more preferably up to 3% of the carrier gas and most preferably up to 1% of the carrier gas is removed from the system after each pass.

The gas velocity is preferably such that the flow in the reactor is laminar in that for example there are no convection eddies opposite to the general direction of flow, and is for example in the range from 0.02 to 1.5 m/s and preferably in the range from 0.05 to 0.4 m/s.

The reaction temperature in the thermally induced polymerization is preferably in the range from 70 to 250° C., more preferably in the range from 80 to 190° C. and most preferably in the range from 90 to 140° C.

The concentration of monomers a) in the monomer solution is typically in the range from 2% to 80% by weight, preferably in the range from 5% to 70% by weight and more preferably in the range from 10% to 60% by weight.

The solubility of monomer a) in water is typically at least 1 g/100 g of water, preferably at least 5 g/100 g of water, more preferably at least 25 g/100 g of water and most preferably at least 50 g/100 g of water.

Preferred polymerization inhibitors require dissolved oxygen for optimum performance. Therefore, the polymerization inhibitors may be freed of dissolved oxygen prior to polymerization by inertization, i.e., flowing an inert gas, preferably nitrogen, through them. The oxygen content of the monomer solution prior to polymerization is preferably lowered to less than 1 weight ppm and more preferably to less than 0.5 weight ppm.

The polymerization inhibitors can also be removed by absorption, for example on activated carbon.

The monomer solution is polymerized in the presence of initiators.

The initiators are used in customary amounts, for example in amounts from 0.001% to 5% by weight and preferably from 0.01% to 1% by weight, based on the monomers to be polymerized.

Useful initiators include all compounds which disintegrate into free radicals under the polymerization conditions, examples being peroxides, hydroperoxides, hydrogen peroxide, persulfates, azo compounds and redox initiators. Preference is given to the use of water-soluble initiators.

Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate.

Preferred initiators are azo compounds, examples being 2,2'-azobisisobutyronitrile, 2,2'-azobis(2,4-dimethylvaleronitrile) and 2,2'-azobis(4-methoxy-2,4-dimethyl-valeronitrile), especially water-soluble azo initiators, examples being 2,2'-azobis-{2-[1-(2-hydroxyethyl)-2-imidazolin-2-yl]propane}dihydrochloride, 2,2'-azobis-(2-amidinopropane) dihydrochloride, 2,2'-azobis[2-(2-imidazolin-2-yl)propane] dihydrochloride and 2,2'-azobis[2-(5-methyl-2-imidazolin-2-yl)propane]dihydrochloride. Very particular preference is given to 2,2'-azobis[2-(2-imidazolin-2-yl)propane]dihydrochloride and 2,2'-azobis[2-(5-methyl-2-imidazolin-2-yl)propane]dihydrochloride.

Redox initiators are also further preferred initiators. In redox initiators, the oxidizing component is at least one of the peroxo compounds indicated above and the reducing component is for example ascorbic acid, glucose, sorbose, ammonium bisulfite, ammonium sulfite, ammonium thiosulfate, ammonium hyposulfite, ammonium pyrosulfite, ammonium sulfide, alkali metal bisulfite, alkali metal sulfite, alkali metal thiosulfate, alkali metal hyposulfite, alkali metal pyrosulfite, alkali metal sulfide or sodium hydroxymethylsulfoxylate. The reducing component in the redox catalyst is preferably ascorbic acid or sodium pyrosulfite. Based on the amount of monomers used in the polymerization, for example from $1 \times 10^{-5}$ to 1 mol % is used of the reducing component of the redox catalyst.

It is particularly preferable to induce the polymerization through the action of high energy radiation, in which case it is customary to use photoinitiators as initiator. Useful photoinitiators include for example α-splitters, H-abstracting systems or else azides. Examples of such Initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds, such as the free radical formers mentioned above, substituted hexaarylbisimidazoles or acylphosphine oxides, especially 2-hydroxy-2-methylpropio-phenone (Darocure® 1173). Examples of azides are 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methyl-cyclohexanone.

Particularly preferred initiators are azo initiators, such as 2,2'-azobis[2-(2-imidazolin-2-yl)propane]dihydrochloride and 2,2'-azobis[2-(5-methyl-2-imidazolin-2-yl)propane]dihydrochloride, and photoinitiators, such as 2-hydroxy-2-methylpropiophenone and 1-[4-(2-hydroxyethoxy)phenyl]-2-hydroxy-2-methyl-1-propan-1-one, redox initiators, such as sodium persulfate/hydroxymethylsulfinic acid, ammonium peroxodisulfate-hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and also mixtures thereof.

The pH of the monomer solution is not decisive. But the pH of the polymer of the present invention can be adjusted to the desired range, dictated by product requirements, via the pH of the monomer solution. For example, polymers for cosmetic applications should typically have a pH of around 7.

The reaction space of the polymerization reactor can be carried out in overpressure or in underpressure, an underpressure of up to 100 mbar below ambient being preferred.

The polymerization rate and the drying rate typically have different temperature dependencies. This can mean, for example, that the droplets dry before the desired conversion has been achieved. It is therefore advantageous to control the reaction rate and the drying rate separately.

The drying rate can be controlled via the relative humidity of the inert gas. The relative humidity of the inert gas is generally less than 90%, preferably less than 60% and more preferably less than 30%. Relative humidity here refers to the quotient of water vapor partial pressure and maximum water vapor partial pressure (saturation) at a given temperature multiplied by 100%.

The polymerization rate can be controlled through the identity and amount of the initiator system used.

The use of azo compounds or redox initiators as initiators is advantageous for directing the rate of polymerization. The starting characteristics of the polymerization are better directable with azo compounds or redox initiators via the choice of initiator, initiator concentration and reaction temperature than for example with pure peroxide initiators.

The carrier gas is advantageously preheated to the reaction temperature upstream of the reactor.

Photoinitiators are particularly advantageous. When photoinitiators are used, the drying rate can be controlled to the desired value via the temperature without thereby significantly influencing the free-radical formation process at the same time.

The reaction offgas, i.e., the carrier gas leaving the reaction space, can be cooled down in a heat exchanger for example. Suitable heat exchangers are direct heat exchangers, such as scrubbers, and indirect heat exchangers, such as condensers. Water and unconverted monomer condense in the process. Thereafter, the reaction offgas can be at least partially reheated and returned into the reactor as recycle gas. Preferably, the recycle gas is cooled down such that the cooled recycle gas has the water vapor fraction desired for the reaction. A portion of the reaction offgas can be removed from the system and replaced by fresh carrier gas, in which case unconverted monomers comprised in the reaction offgas can be separated off and recycled.

Particular preference is given to an integrated energy system whereby a portion of the heat rejected in the cooling of the offgas is used to heat up the cycle gas.

The reactors can be trace heated. Any trace heating is adjusted such that the wall temperature is not less than 5° C. above reactor internal temperature and condensation at reactor walls is reliably avoided.

The reaction product is preferably transferred in a fluidized state into at least one of the process steps drying, agglomeration and/or postcrosslinking.

The polymeric particles are subsequently dried and optionally agglomerated and/or postcrosslinked.

Useful agglomeration assistants include water and water-miscible organic solvents, such as alcohols tetrahydrofuran and acetone; water-soluble polymers can be used in addition.

Useful postcrosslinkers include compounds comprising at least two groups capable of forming covalent bonds with the carboxylate groups of the hydrogel. Useful compounds include for example alkoxysilyl compounds, polyaziridines, polyamines, polyamido-amines, di- or polyglycidyl compounds, as described in EP-A-0 083 022, EP-A-0 543 303 and EP-A-0 937 736, di- or polyfunctional alcohols, as described in DE-C-33 14 019, DE-C-35 23 617 and EP-A-0 450 922, or β-hydroxyalkylamides, as described in DE-A-102 04 938 and U.S. Pat. No. 6,239,230.

Useful postcrosslinkers are further said to include by DE-A-40 20 780 cyclic carbonates, by DE-A-198 07 502 2-oxazolidone and its derivatives, such as 2-hydroxyethyl-2-oxazolidone, by DE-A-198 07 992 bis- and poly-2-oxazolidinones, by DE-A-198 54 573 2-oxotetrahydro-1,3-oxazine and its derivatives, by DE-A-198 54 574 N-acyl-2-oxazolidones, by DE-A-102 04 937 cyclic ureas, by DE-A-103 34 584 bicyclic amide acetals, by EP-A-1 199 327 oxetanes and cyclic ureas and by WO-A-03/1031482 morpholine-2,3-dione and its derivatives.

A preferred embodiment of the present invention comprises polymerizing in laminar cocurrent and drying in a turbulent gaseous stream. The polymerization is preferably initiated by photoinitiators. The droplets are preferably led past the sources of radiation to initiate the polymerization in a laminar flow of inert gas. The sources of radiation are disposed outside the reaction zone, of course. The laminar flow prevents contact between the monomer droplets and hence prevents uncontrolled sticking together. The inert gas temperature is preferably less than 80° C., more preferably less than 60° C., most preferably less than 40° C. and typically not less than 20° C.

After a monomer conversion of typically at least 50%, preferably at least 60%, more preferably at least 70% and most preferably at least 80%, the water-absorbing particles are mechanically sufficiently robust and are dried in a turbulent gaseous stream. To this end, the reactor is fed with a preheated stream of inert gas, the inert gas rate being chosen such that a turbulent flow of inert gas results. The turbulent gaseous flow has a Reynolds number (Re) of above 2300, preferably of above 3000, more preferably of above 4000 and most preferably of above 5000. The turbulent stream of inert gas improves the heat transfer and speeds drying. The inert gas used for drying is advantageously preheated upstream of the reactor to a temperature in the range from 70 to 250° C., preferably in the range from 90 to 190° C. and more preferably in the range from 110 to 160° C.

The transfer from the polymerization stage into the drying stage is effected through the water-absorbing polymeric particles free-falling from the upper into the lower portion of the reactor. In the lower portion of the reactor, the water-absorbing polymeric particles are dried and the monomer conversion is enhanced.

The combination of a photopolymerization in a laminar flow of inert gas and of drying in a turbulent flow of inert gas makes it possible to conduct polymerization and drying in one apparatus and at the same time for polymerization and drying to be decoupled and separately optimized.

The present invention further provides water-absorbing polymeric particles obtainable by the process of the present invention.

The present invention further provides postcrosslinked water-absorbing dropletization polymers. Polymeric particles producible by dropletization polymerization in the gas phase, in particular by thermally induced polymerization, have an essentially continuous surface with or without depressions. The essentially continuous surface is due to the droplet shape of the dropletized monomer solution. The monomers in a droplet start to polymerize from the droplet surface, forming a polymeric skin which is still soft and deformable. At the same time, water starts to evaporate out of the droplet causing the polymeric skin to become inflated. In the process, the polymeric skin may also break open in some instances, and this can lead to discontinuities in the continuous surface. This inflating enhances the porosity and hence the initial swell rate of the polymeric particles. As the polymerization continues, the polymeric particles may, as long as the polymer is still plastically deformable, collapse as a result of the mass loss through evaporation. The surface of a collapsed polymeric particle will therefore be wrinkled as well as essentially continuous.

As a consequence of the relatively large droplet size produced by dropletization, the droplets dry only slowly during the polymerization. This gives polymeric particles of high water content and high monomer conversion. The polymeric particles have high absorbency under load and only low extractable fractions. But the advantageous properties are destroyed again by mechanical stress, for example due to afterdrying in a paddle dryer or plowshare mixer. It is therefore important that afterdrying be carried out as gently as possible, for example in a fluidized bed dryer.

The water-absorbing polymeric particles of the present invention typically have a Centrifuge Retention Capacity (CRC) of from 20 to 80 g/g, preferably at least 30 g/g and more preferably at least 40 g/g. Centrifuge Retention Capacity (CRC) is determined by EDANA (European Disposables and Nonwovens Association) recommended test method No. 441.2-02 "Centrifuge retention capacity".

The water-absorbing polymeric particles of the present invention typically have an Absorbency Under Load 0.3 psi (2.07 kPa) of from 10 to 30 g/g, preferably at least 15 g/g and more preferably at least 20 g/g. Absorbency Under Load (AUL) is determined by EDANA (European Disposables and Nonwovens Association) recommended test method No. 442.2-02 "Absorption under pressure".

The extractables content of the water-absorbing polymeric particles of the present invention is typically less than 15% by weight, preferably less than 10% by weight and more preferably less than 5% by weight. Extractables are determined in accordance with EDANA (European Disposables and Nonwovens Association) recommended test method No. 470.2-02 "Extractables".

The water content of the water-absorbing polymeric particles of the present invention is typically less than 15% by weight, preferably less than 10% by weight and more preferably less than 5% by weight. Water content is determined in accordance with EDANA (European Disposables and Nonwovens Association) recommended test method No. 430.2-02 "Moisture content".

The present invention further provides processes for producing hygiene articles, in particular diapers, comprising the use of water-absorbing polymeric particles produced by the abovementioned process.

The present invention further provides for the use of the water-absorbing polymeric particles of the present invention in hygiene articles, for thickening wastes, in particular medical wastes, or as a water-retaining agent in agriculture.

The present invention further provides hygiene articles comprising an absorbent layer comprising from 30% to 100% by weight, preferably from 60% to 100% by weight, more preferably from 70% to 100% by weight, even more preferably from 80% to 100% by weight and most preferably from 90% to 100% by weight of water-absorbing polymeric particles according to the present invention, the envelope surrounding the absorbent layer not included of course.

The present invention further provides apparatus for producing polymers by dropletization polymerization in the gas phase, comprising i) a heatable reaction space,
ii) at least one apparatus for droplet generation in the upper region of the reaction space i),
iii) selectively at least one carrier gas feed, preferably in the upper portion of the reaction space i),
iv) selectively at least one carrier gas preheater,
v) selectively at least one carrier gas outlet, preferably in the lower portion of the reaction space i),
vi) selectively at least one apparatus for recycling at least a portion of the removed carrier gas from the carrier gas outlet v) to the carrier gas feed iii),
vii) selectively at least one source of radiation, preferably in the upper part of the reaction space i),
viii) a fluidized bed apparatus outside of the reaction space i),
ix) selectively an apparatus for transporting water-absorbing polymeric particles in the fluidized state from the reaction space i) into the fluidized bed apparatus viii),
x) selectively at least one apparatus for agglomeration or postcrosslinking, and
xi) selectively at least one apparatus for transporting water-absorbing polymeric particles in the fluidized state from the previous process step into the agglomeration and/or postcrosslinking apparatus x), the upper region of the reaction space being the upper 50%, preferably the upper 30% and particularly the upper 10% of the reaction space volume and the lower region of the reaction space being the lower 50%, preferably the lower 30% and particularly the lower 10% of the reaction space volume.

The apparatus vi) comprises for example a compressor, particularly a ventilator, a flow rate meter and a closed loop controllable valve. The compressor increases the pressure of the carrier gas and thus makes it possible for it to be recycled to the carrier gas feed iii). The flow rate meter and the valve can be used to adjust the amount of carrier gas recycled.

The apparatus ix) and xi) may be for example a fluidized bed apparatus or a pneumatic conveyor. It is similarly possible for sequential process steps to be disposed one above the other, so that the water-absorbing polymeric particles can free-fall from the previous into the subsequent process step. In this case, the apparatus ix) or xi) is the connection between the process steps.

The apparatus for agglomeration and/or postcrosslinking is preferably a fluidized bed apparatus.

One preferred embodiment is depicted in FIG. 1. The reference numerals have the following meanings:

A: dropletization reactor

B: integrated fluidized bed apparatus

C: cyclone

1: inlet

2: carrier gas (for reaction)

3: carrier gas (for fluidized bed)

4: agglomeration assistant/postcrosslinker

5: offgas and fines

6: fines recycling

7: offgas

8: product takeoff

FIG. 1 shows a mutually superposed arrangement for reaction space i) and fluidized bed drying apparatus viii). The fluidized bed apparatus may additionally be used for agglomerating and/or postcrosslinking. Fines entrained in the carrier gas are collected in a cyclone and recycled.

Figure 2:
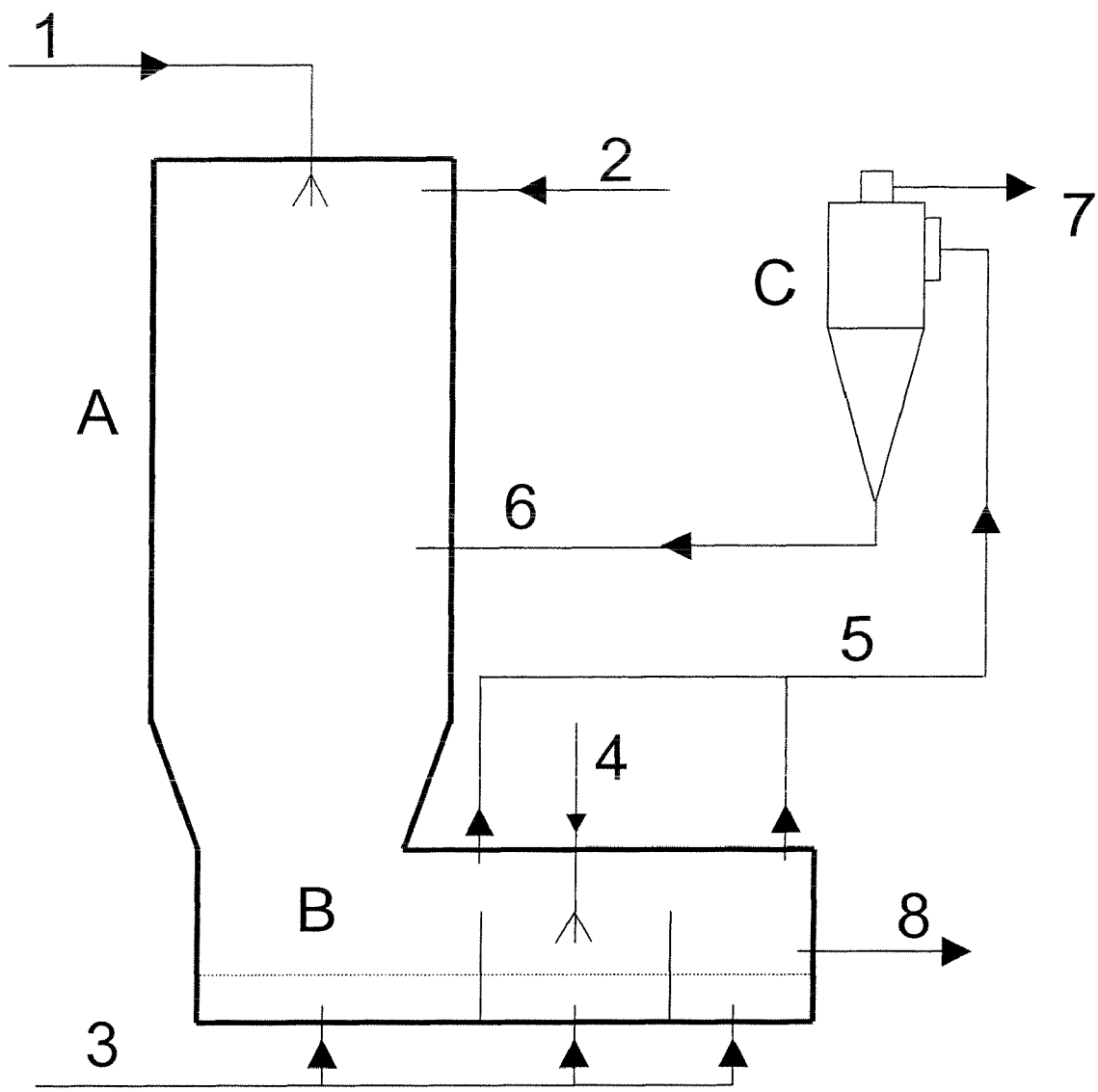

One further preferred embodiment is depicted in FIG. 2. The reference numerals have the abovementioned meanings, B being a fluidized bed battery.

The transportation apparatus xi) in FIG. 2 is a fluidized bed apparatus. The water-absorbing polymeric particles pass via overflow weirs into second and third fluidized bed apparatus. The second and third fluidized bed apparatus are the apparatus for agglomeration and/or postcrosslinking x). The height of the weirs makes it possible to adjust the residence times. It is preferable to set different temperatures in the successive fluidized bed apparatus, the temperatures being individually matched to the offices to be carried out in the fluidized beds.

In FIG. 2, the mixing of the water-absorbing polymeric particles with the agglomeration assistant and/or postcrosslinking agent and the thermal aftertreatment are separated. It will be appreciated that both the steps can also be carried out in a fluidized bed apparatus.

As FIGS. 1 and 2 show by way of example, the process of the present invention provides a simple way to recycle fines.

The present invention further provides apparatus for producing polymers by dropletization polymerization, comprising i) a reaction space,
ii) at least one apparatus for droplet generation in the upper region of the reaction space i),
iii) selectively at least one carrier gas feed in the upper portion of the reaction space i),
iv) selectively at least one carrier gas feed between the upper portion and the lower portion of the reaction space i),
v) selectively at least one carrier gas preheater for the carrier gas feed iv),
vi) selectively at least one carrier gas outlet, preferably in the lower portion of the reaction space i),
vii) selectively at least one apparatus for recycling at least a portion of the removed carrier gas from the carrier gas outlet vi) to the carrier gas feed iii) and/or carrier gas feed iv),
viii) at least one source of radiation in the upper portion of the reaction space i),
ix) selectively at least one apparatus for agglomeration and/or postcrosslinking, and
x) selectively at least one apparatus for transporting water-absorbing polymeric particles in the fluidized state from the reaction space i) into the agglomeration and/or postcrosslinking apparatus ix), the upper region of the reaction space being the upper 50%, preferably the upper 30% and particularly the upper 10% of the reaction space volume and the lower region of the reaction space being the lower 50%, preferably the lower 30% and particularly the lower 10% of the reaction space volume.

Figure 3:
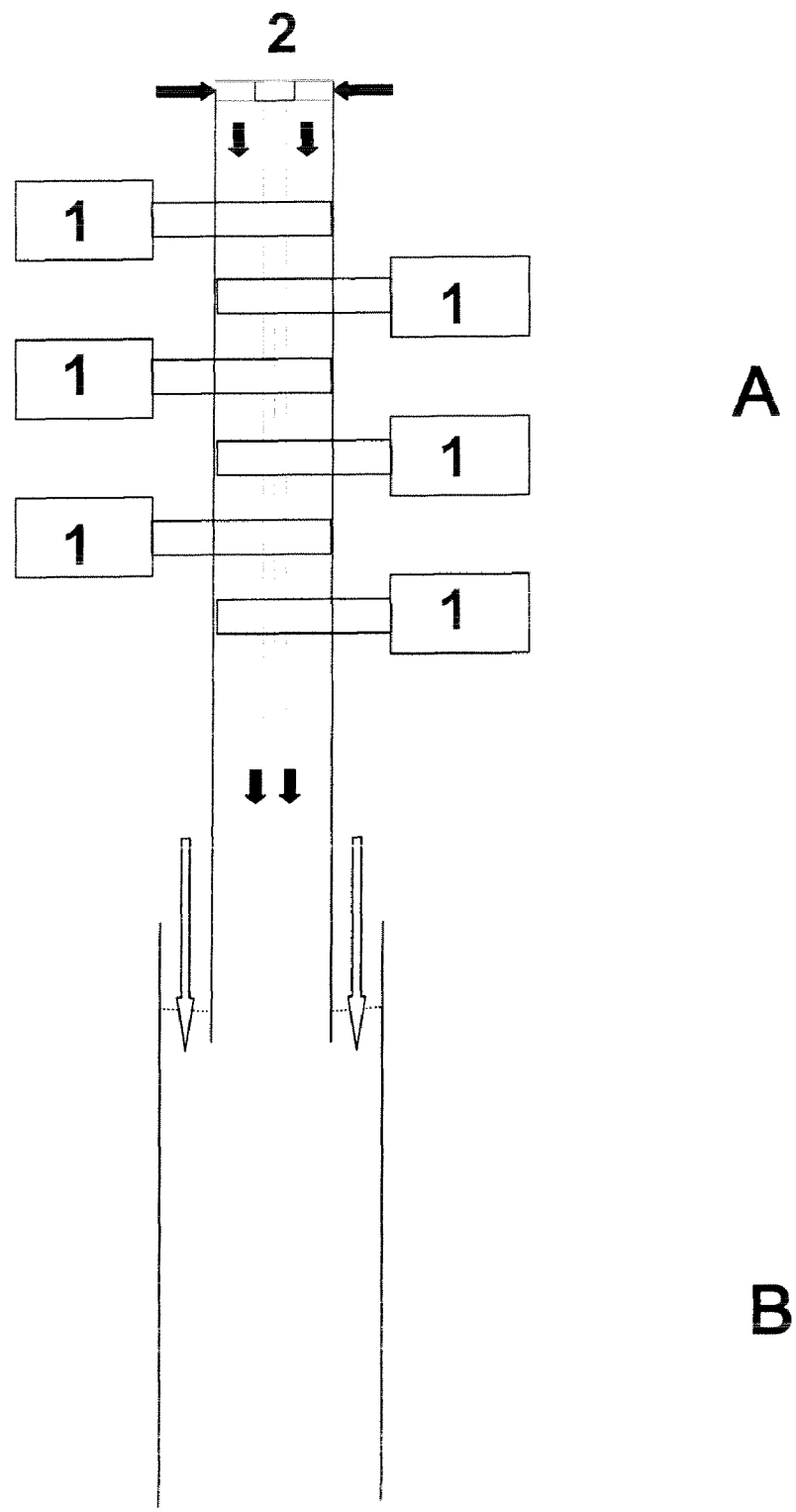
FIG. 3 is a schematic illustrating an apparatus for producing water-absorbing polymer particles by dropletization polymerization.

A preferred embodiment is depicted in FIG. 3. The reference numerals have the following meanings:

A: upper reaction space

B: lower reaction space

1: source of radiation

2: droplet generator

In FIG. 3, droplets are produced from a monomer solution, preferably by dropletization, at the upper end of the reaction space. The droplets free-fall through the upper reaction space, the polymerization being initiated through suitable sources of radiation. Examples of suitable sources of radiation are UV sources, IR sources, X-ray sources, electron beam sources. The bulk of the polymerization takes place in the upper portion. The gas flow is laminar, i.e., the droplets are not whirled about. The lower reaction space is fed with preheated carrier gas, the gas flow in the lower reaction space is turbulent. The postreaction and drying takes place in the lower reaction space.

In FIG. 3, the solid arrows indicate a non-preheated stream of inert gas and the non-solid arrows indicate a preheated stream of inert gas.

The embodiments depicted in FIGS. 1 to 3 are mere examples of dropletization-polymerization apparatuses according to the present invention and do not limit the technical teaching of the present invention in any way.

To determine the quality of postcrosslinking, the dried water-absorbing polymeric particles are tested using the test methods described hereinbelow.

Methods:

The measurements should be carried out, unless otherwise stated, at an ambient temperature of 23±2° C. and a relative humidity of 50±10%. The water-absorbing polymeric particles are thoroughly mixed through before measurement.

Water Content

The water content of the water-absorbing polymeric particles is determined in accordance with EDANA (European Disposables and Nonwovens Association) recommended test method No. 430.2-02 "Moisture content".

Centrifuge Retention Capacity (CRC)

Centrifuge Retention Capacity of the water-absorbing polymeric particles is determined by EDANA (European Disposables and Nonwovens Association) recommended test method No. 441.2-02 "Centrifuge retention capacity".

Absorbency Under Load (AUL)

Absorbency Under Load of the water-absorbing polymeric particles is determined by EDANA (European Disposables and Nonwovens Association) recommended test method No. 442.2-02 "Absorption under pressure".

Extractables

The extractable fractions of the water-absorbing polymeric particles are determined in accordance with EDANA (European Disposables and Nonwovens Association) recommended test method No. 470.2-02 "Extractables".

EDANA test methods are obtainable for example at European Disposables and Nonwovens Association, Avenue Eugene Plasky 157, B-1030 Brussels, Belgium.

EXAMPLES

Example 1

12 kg of sodium acrylate (37.5% by weight solution in water) and 1.1 kg of acrylic acid were mixed with 3 kg of water and 9 g of 15-tuply ethoxylated trimethylolpropane triacrylate. The solution was admixed with initiators and then dropletized into a heated nitrogen-filled dropletization tower (170° C., 12 m high, 2 m wide, gas velocity 0.1 m/s in cocurrent). The metering rate was 16 kg/h. The dropletizer plate had 37 drilled holes each 170 μm in size. The diameter of the dropletizer plate was 65 mm. The initiators used were 2,2-azobis[2-(2-imidazolin-2-yl)propane]dihydrochloride and 2,2-azobis(2-amidinopropane) dihydrochloride. The concentration of each initiator was 0.2% by weight, based on the monomer. The admixing of the initiators to the monomer solution took place via a static mixer just upstream of the dropletizer with the initiators in a 2% aqueous solution.

The water-absorbing polymeric particles collecting on the bottom of the dropletization tower had a water content of 16.5% by weight.

The polymeric particles were dried in a fluidized bed dryer at 80° C. for two hours.

The dried water-absorbing polymeric particles had the following properties:

| | |
|---|---|
| CRC: | 56.5 g/g |
| AUL0.3 psi | 20.5 g/g |
| Extractables | 10.6% by weight |
| Water content | 3.5% by weight |

Example 2 (Comparative)

Example 1 was repeated. The water-absorbing polymeric particles collecting at the bottom of the dropletization tower were dried in a plowshare mixer.

The dried water-absorbing polymeric particles had the following properties:

| | |
|---|---|
| CRC: | 52.7 g/g |
| AUL0.3 psi | 14.4 g/g |
| Extractables | 14.6% by weight |
| Water content | 3.7% by weight |

The invention claimed is:

1. A process for producing water-absorbing polymeric particles by dropletization polymerization in a gas phase, wherein a monomer solution is dropletized at a speed of less than 0.2 m/s, which comprises the polymeric particles after the polymerization being dried and optionally agglomerated and/or postcrosslinked, the drying being carried out in a fluidized bed.

2. The process according to claim 1 wherein the polymeric particles are transferred in the fluidized state from the polymerization into at least one of the process steps of drying, agglomeration, and postcrosslinking.

3. The process according to claim 2 wherein the fluidized state is brought about by a fluidized bed.

4. The process according to claim 2 wherein the fluidized state is brought about by pneumatic conveying.

5. The process according to claim 2 wherein the fluidized state is brought about by free fall.

6. The process according to claim 1 wherein the polymeric particles are in a fluidized state during agglomeration and/or postcrosslinking.

7. The process according to claim 6 wherein the agglomeration and/or postcrosslinking is carried out in a fluidized bed.

8. The process according to claim 1 wherein the polymerization is initiated by photoinitiators.

9. The process according to claim 8 wherein the polymerization is carried out up to a monomer conversion of at least 50% at a gas temperature of less than 80° C.

10. Water-absorbing polymeric particles in powder form prepared according to the process of claim 1.

11. A hygiene article comprising water-absorbing polymeric particles prepared according to claim 1.

12. Apparatus for producing water-absorbing polymeric particles by a dropletization polymerization comprising an apparatus for generating droplets at a speed of less than 0.2 m/s in which the polymeric particles after the polymerization are dried and optionally agglomerated and/or postcrosslinked, wherein the apparatus for drying is a fluidized bed apparatus.

13. The apparatus according to claim 12, comprising a connection which connects the polymerization and at least one of the process steps of drying, agglomeration, or postcrosslinking, and in which the polymeric particles can be transported in a fluidized state.

14. The apparatus according to claim 13 wherein the connection is a fluidized bed apparatus.

15. The apparatus according to claim 13 wherein the connection is a pneumatic conveyor.

16. The apparatus according to claim 13 wherein the connection is a tube whose diameter and inclination are such that the openings at the ends of the tube partially or completely overlap in the vertical.

17. The apparatus according to claim 12 wherein the agglomeration and/or postcrosslinking is carried out in a fluidized bed apparatus.

18. A method of thickening a waste comprising contacting the waste with water-absorbing polymeric particles prepare according to claim 1.

19. An agricultural water-retaining agent comprising water-absorbing particles prepared according to claim 1.

20. The process of claim 1 wherein the monomer solution is dropletized at a speed of less than 0.1 m/s.

* * * * *